United States Patent
Maier

(10) Patent No.: US 12,357,415 B2
(45) Date of Patent: Jul. 15, 2025

(54) METHOD FOR MARKING AN ENTRY POSITION FOR AN INJECTION APPARATUS IN INTERVENTIONAL MR IMAGING

(71) Applicant: Siemens Healthcare GmbH, Erlangen (DE)

(72) Inventor: Florian Maier, Buckenhof (DE)

(73) Assignee: Siemens Healthineers AG, Erlangen (DE)

( * ) Notice: Subject to any disclaimer, the term of this patent is extended or adjusted under 35 U.S.C. 154(b) by 434 days.

(21) Appl. No.: 17/836,157

(22) Filed: Jun. 9, 2022

(65) Prior Publication Data
US 2022/0395349 A1 Dec. 15, 2022

(30) Foreign Application Priority Data
Jun. 9, 2021 (DE) .......................... 102021205811.6

(51) Int. Cl.
- *A61B 90/00* (2016.01)
- *A61B 5/055* (2006.01)
- *G01R 33/48* (2006.01)
- *G01R 33/56* (2006.01)
- *G01R 33/563* (2006.01)

(52) U.S. Cl.
CPC .............. *A61B 90/37* (2016.02); *A61B 5/055* (2013.01); *G01R 33/4818* (2013.01); *G01R 33/5608* (2013.01); *G01R 33/56333* (2013.01); *A61B 2090/374* (2016.02)

(58) Field of Classification Search
CPC .................................................... A61B 90/37
See application file for complete search history.

(56) References Cited

U.S. PATENT DOCUMENTS

| | | | |
|---|---|---|---|
| 6,972,022 B1* | 12/2005 | Griffin | A61B 90/39 606/116 |
| 2017/0014203 A1* | 1/2017 | De Mathelin | A61B 5/066 |

FOREIGN PATENT DOCUMENTS

DE 102019211870 A1 9/2020

OTHER PUBLICATIONS

McKesson Medical-Surgical: "Surgical Skin Marker Purple Bold Tip Sterile"; URL: https://mms.mckesson.com/product/947860/Viscot-Industries-VF400SR-25 [recherchiert und aufgerufen am Jan. 2, 2022].

(Continued)

*Primary Examiner* — Joseph M Santos Rodriguez
(74) *Attorney, Agent, or Firm* — Banner & Witcoff Ltd.

(57) ABSTRACT

A method for marking an entry position for an injection apparatus on a surface of a patient positioned inside a patient receiving region of a magnetic resonance device. The method includes providing a virtual entry position, introducing a marking apparatus into the patient receiving region, acquiring time-resolved MR image data from the marking apparatus by the magnetic resonance device, ascertaining a current position of the marking apparatus based on the time-resolved MR image data, iteratively changing the current position of the marking apparatus using the virtual entry position and the current position, and delivering the liquid from the marking apparatus when the current position matches the virtual entry position.

16 Claims, 3 Drawing Sheets

(56) References Cited

OTHER PUBLICATIONS

Immersion Wellness Organization: "Considerations for Selecting Mammography Skin Markers Suppliers"; URL: https://www.eactaiccva2014.org/health/considerations-selecti ng-mammographyskin-markersuppliers/ [recherchiert und aufgerufen am Jan. 2, 2022].

\* cited by examiner

METHOD FOR MARKING AN ENTRY POSITION FOR AN INJECTION APPARATUS IN INTERVENTIONAL MR IMAGING

TECHNICAL FIELD

The disclosure relates to a method and to a marking apparatus for marking an entry position for an injection apparatus during the course of interventional Magnetic resonance (MR) imaging.

BACKGROUND

With minimally invasive medical procedures, medical instruments (e.g., catheters and/or surgical needles) are introduced into a patient, wherein, customarily, image monitoring of the procedure takes place. Image monitoring enables the acquisition of images in which the medical instrument is rendered visible in relation to its anatomical surroundings. While, conventionally, X-ray imaging has been used for image monitoring of minimally invasive medical interventions (i.e., fluoroscopy), it has also been proposed in the meantime that magnetic resonance imaging devices are used for image monitoring. This is typically referred to as interventional MR imaging. When what are known as closed magnetic resonance devices are used, which have a main magnet with a cylindrical patient receiving region in which the homogeneity volume is located, the space being worked in is very confined, so any support for the person carrying out the intervention is useful.

One specific type of medical instrument, which is frequently used for minimally invasive medical interventions, is surgical needles, which are used, for example, for biopsies, ablation or brachytherapy. With respect to surgical needles, it has also already been proposed that they be propagated with magnetic resonance real-time control. For this it is necessary that the surgical needle to be positioned is introduced at an entry position defined in a planning step, and preferably with a particular angle of entry, in order to then be advanced along the thus defined trajectory to a target position, in particular to a lesion.

In the planning phase the anatomical boundary conditions and technical limitations, which result due to support of the patent in the patient receiving region, are taken into account. Anatomical boundary conditions relate in particular to the localization not only of the lesion, but also of bones, vessels and other structures that are to be spared. The planning, in particular the definition of the entry position, the trajectory and the target position, can be carried out, for example, on MR image data acquired with the magnetic resonance device, preferably three-dimensional MR image data.

For a time-efficient implementation of the minimally invasive intervention, which is as sparing and pain-free as possible for the patient, it is indispensable that the entry position and optionally also the angle of entry in accordance with the planning can be found without subsequent repositioning.

Approaches have already been proposed in the prior art for implementing this with a magnetic resonance device. Firstly, manual marking and representation of the entry position and of the angle of entry by means of the finger of a person carrying out the intervention is possible. For this purpose, the finger of the radiologist is positioned with image monitoring, real-time MR imaging therefore, at the entry position in the same way as the surgical needle should subsequently be introduced. However, owing to the large diameter of the finger compared to the diameter of the surgical needle, accurate planning is thus barely possible. The entry position thus identified is then marked with the aid of a pen and/or a sticker visible in MR image data. It is likewise known that a grid visible in MR image data is applied to the surface of the patient and the entry position relative to the grid is determined, for example by counting grid lines. In a different approach it has been proposed that the position of the entry position in the longitudinal direction of the patient receiver is marked by means of a laser point or, generally, light patterns projected onto the surface of the patient. Even after planning and fixing the entry position on the basis of MR image data these approaches allow only inaccurate marking. As a result, the entry position for the medical instrument used in a minimally invasive medical intervention can deviate from the fixed entry position, so the risk and the duration of the minimally invasive medical intervention increase.

SUMMARY

The disclosure is based on an object of disclosing support for a person carrying out a minimally invasive medical intervention, image-assisted by MR imaging, that is improved by comparison.

The disclosed marking apparatus comprises a tubular housing apparatus made from MR-visible material surrounding a hollow region oriented in the axial direction, a liquid apparatus arranged inside the hollow region at a first longitudinal end of the housing apparatus designed to receive and/or deliver a liquid, and a portioning apparatus arranged inside the hollow region and designed to control a volume of the liquid apparatus to receive and/or deliver the liquid.

MR-visible material typically comprises hydrogen protons, which generate signal in the course of MR imaging. MR-visible material is typically characterized in that it can be identified in MR image data acquired with a magnetic resonance device, in particular has a contrast with the surroundings.

The housing apparatus may have a hollow cylindrical shape. The housing apparatus typically has an elongate shape, with the spatial extent in the axial direction, in the elongate direction therefore, typically being at least three times, preferably at least five times, particularly preferably at least eight times as large as the spatial extent of the housing apparatus in a plane perpendicular thereto. The hollow region typically has an elongate shape, with the spatial extent in the axial direction, in the elongate direction therefore, typically being at least three times, preferably at least five times, particularly preferably at least eight times as large as the spatial extent of the hollow region in a plane perpendicular thereto.

The first longitudinal end is typically an end of the marking apparatus in the axial direction. The hollow region is preferably free from material. The portioning apparatus and the liquid apparatus are preferably at least partially arranged inside the hollow region. The acquisition and/or delivery of the liquid preferably takes place via the first longitudinal end.

The portioning apparatus typically has an elongate shape, with the spatial extent in the axial direction, in the elongate direction therefore, typically being at least three times, preferably at least five times, particularly preferably at least eight times as large as the spatial extent of the portioning apparatus in a plane perpendicular thereto. The first longitudinal end is typically free from the portioning apparatus.

The liquid apparatus is arranged at the first longitudinal end. As a result, the liquid of the liquid apparatus can be supplied via the first longitudinal end and/or be delivered from it via the first longitudinal end. The supply and/or the delivery are typically controlled by means of the portioning apparatus. The portioning apparatus accordingly enables filling of the liquid apparatus with liquid prior to use of the marking apparatus for marking an entry position. In particular, the liquid apparatus can be filled rapidly, so a fresh liquid can be used for each marking. As a result, the liquid can in particular comprise substances, which are subject to decay over time, such as contrast medium and/or radiopharmaceuticals. The liquid can be in the form of a gel.

The marking apparatuses, in particular the liquid apparatus, are typically configured in such a way that when the first longitudinal end touches a surface, in particular a surface or the skin of a patient, the liquid can be delivered with the support of the portioning apparatus. The liquid can be used for marking a point and/or an entry position on a surface, in particular on the skin, of the patient. The portioning apparatus preferably enables a precise and selective delivery of the liquid via the first longitudinal end.

The MR-visible material of the housing apparatus enables application of the marking apparatus with image monitoring, in particular in combination with real-time MR imaging, during the course of marking an entry position. A virtual entry position can have been planned in advance already on the basis of MR image data. The disclosed marking apparatus can be used especially effectively in particular in combination with time-resolved MR image data, in particular with real-time MR imaging, by taking into account the virtual entry position for marking the actual entry position on the surface of the patient. The visibility of the marking apparatus in MR image data, in particular also with real-time MR imaging, is fixed by the choice of material. Owing to the elongate shape of the marking apparatus, the apparatus can be particularly well oriented, by means of time-resolved MR image data it can be observed and/or precisely positioned. Consequently, an entry position can be particularly accurately marked, and this renders a minimally invasive medical intervention particularly safe. Owing to the simple construction the marking apparatus is inexpensive to manufacture. The marking apparatus can be designed as a product for one-time use. The marking apparatus is preferably sterile in this case.

One aspect of the marking apparatus provides that the hollow region is cylindrical. The housing apparatus is accordingly preferably at least partially configured as a hollow cylinder. A cylindrical hollow region has a round cross-section perpendicular to the axial direction. As a result, the marking apparatus can be manufactured particularly easily.

One aspect of the marking apparatus provides that the housing apparatus has a wall thickness that reduces in the direction of the first longitudinal end. The diameter of the hollow region is preferably constant for the entire length of the marking apparatus in the axial direction. The outer shape of the marking apparatus preferably tapers in the direction of the first longitudinal end in the axial direction. This enables better positioning of the marking apparatus at a predefined position, in particular at a virtual entry position, since a visual check of the marking apparatus is more easily possible, in particular compared with manual marking by means of a finger.

One aspect of the marking apparatus provides that the housing apparatus has a cylindrical part surrounding a first hollow region and a truncated cone-shaped part adjoining the cylindrical part in the axial direction surrounding a second hollow region at the first longitudinal end and the hollow region comprises the first hollow region and the second hollow region. The hollow region can be composed of the first hollow region and the second hollow region. The first hollow region and the second hollow region can merge continuously into each other and/or be connected together free from an interruption. The truncated cone-shape part of the housing apparatus preferably has a shape tapering toward the first longitudinal end. This enables better positioning of the marking apparatus at a predefined position, in particular at a virtual entry position, since a visual check of the marking apparatus is more easily possible, in particular compared with manual marking by means of fingers.

One aspect of the marking apparatus provides that the second hollow region comprises the liquid apparatus. The liquid apparatus and the second hollow region are preferably arranged at the first longitudinal end. According to this aspect, the liquid apparatus is a section of the hollow region. The liquid apparatus can correspond to the second hollow region. The liquid apparatus can comprise the second hollow region and a part of the first hollow region. The volume of the liquid apparatus is preferably determined via the volume of the liquid to be acquired and/or delivered. The surface tension of the liquid preferably enables a spatial limitation of the liquid apparatus. This enables a flexible volume of the liquid apparatus, which can be filled by means of the portioning apparatus. In addition, a marking apparatus of this kind is particularly easy to manufacture.

One aspect of the marking apparatus provides that the portioning apparatus is arranged inside the first hollow region. According to this aspect, the length of the portioning apparatus in the axial direction matches at least the length of the first hollow region. The portioning apparatus is typically movably arranged inside the hollow region, in particular the first hollow region. By shifting the position of the portioning apparatus in the axial direction, liquid can be acquired in the first hollow region in a controlled manner via the first longitudinal end and/or liquid can be delivered from the first hollow region in a controlled manner via the first longitudinal end.

One aspect of the marking apparatus provides that in the axial direction the length of the hollow region matches the length of the housing apparatus. The housing apparatus accordingly preferably has a completely tubular shape. A housing apparatus of this kind, and therewith marking apparatus, is particularly simple and inexpensive to manufacture and therewith particularly well suited as a sterile product for one-time use.

One aspect of the marking apparatus provides that the marking apparatus comprising the liquid comprises a contrast medium and/or the liquid is sterile and/or colored. If the liquid is colored, after delivery to a surface of a patient during the course of marking of an entry position the liquid can thus be visually identified by medical staff. This is important in particular at the beginning of the minimally invasive medical procedure since entry position can thus be easily identified by staff. A sterile liquid is advantageous in particular for the avoidance of infections since a minimally invasive medical procedure is carried out at the entry position marked by means of the liquid. A liquid comprising contrast medium can be identified particularly well in MR image data, in particular in time-resolved MR image data acquired during positioning of the marking apparatus, so the marking apparatus can be easily positioned. Similarly, after delivery of the liquid to the surface of a patient it is possible to check particularly effectively whether the marked entry position matches the virtual entry position.

One aspect of the marking apparatus provides that the length of the housing apparatus is variable in the axial direction. In particular, the length of the marking apparatus in the axial direction is variable as a result. This enables a simulation of a length of a medical instrument, such as a catheter and/or a surgical needle, used during a minimally invasive medical procedure following the use of the marking apparatus. If the marking apparatus is used inside the magnetic resonance device, which is also used during a subsequent minimally invasive medical procedure for time-resolved MR imaging, the compatibility of the medical instrument intended for use with the entry position inside the magnetic resonance device can be tested. This enables particularly good preparation for the minimally invasive intervention method, which is safter as a result.

One aspect of the marking apparatus provides that the housing apparatus is telescopic. A tubular housing apparatus of variable length can be configured to be telescopic particularly easily and robustly. In particular, the telescopic form enables a continuous adjustment of the length of the housing apparatus, so the length of a large number of medical instruments can be replicated.

One aspect of the marking apparatus provides that the portioning apparatus has flush external dimensions for the hollow region and is movably arranged inside the hollow region. This enables particularly robust and intuitive control of the volume of the liquid apparatus for acquisition and/or delivery of the liquid.

One aspect of the marking apparatus provides that the portioning apparatus has a widening at the longitudinal end of the housing apparatus opposing the first longitudinal end, which widening is arranged outside of the housing apparatus. The widening typically has a larger diameter than the hollow region. The widening can be used by medical staff as a support surface for a finger for manual operation of the portioning apparatus and therewith for control of the volume of the liquid apparatus for delivery of the liquid, in particular if the support surface is moved in the axial direction in the direction of the first longitudinal end. The widening can be used by medical staff as a lever for acquisition of the liquid, in particular if the support surface is moved away from the first longitudinal end in the axial direction.

The disclosure starts from a method for marking an entry position for an injection apparatus on a surface of a patient positioned inside a patient receiving region of a magnetic resonance device, comprising the following method steps:
provision of a virtual entry position,
introducing a disclosed marking apparatus into the patient receiving region,
acquisition of time-resolved MR image data from the marking apparatus by means of the magnetic resonance device,
ascertainment of a current position of the marking apparatus based on the time-resolved MR image data,
iterative change in the current position of the marking apparatus using the virtual entry position and the current position,
delivery of the liquid from the marking apparatus when the current position matches the virtual entry position.

The method is typically carried out in preparation for interventional MR imaging.

The patient is preferably supported inside a patient receiving region of a magnetic resonance device in such a way that the target entry position is arranged inside an examination region. The examination region is the section of the patient receiving region, which is characterized in that the magnetic resonance device is designed to capture MR image data of this section.

The entry position is typically the entry point of the medical instrument on the surface, in particular on the skin, of the patient, in order to reach the target position with the medical instrument. The entry position to be marked and to be used during the course of the minimally invasive intervention is typically located in the coordinate system of the patient and/or of the magnetic resonance device, in particular in a real spatial coordinate system. The virtual entry position is typically present in the coordinate system of the MR image data. The virtual entry position typically corresponds to the target entry position, identified during planning and/or based on MR image data acquired with the magnetic resonance device. Planning preferably takes place before the beginning of the disclosed method. The provision of the virtual entry position can comprise an acquisition of MR image data, in particular of three-dimensional MR image data, of the examination region. The provision of the virtual entry position can comprise an identification of a target position and a trajectory for a medical instrument for reaching the target position starting from the virtual entry position. The provision of the virtual entry position can comprise a determination of the virtual entry position based on MR image data, with it being possible for determination to take place manually by medical staff and/or automatically. The provision of the virtual entry position can comprise a provision of MR image data comprising a marker at the virtual entry position.

The disclosed method provides that the virtual entry position is transferred from the coordinate system of the MR image data into the real spatial coordinate system of the patient and/or of the magnetic resonance device, is marked in this by delivery of the liquid from the marking apparatus. The method provides an iterative approach of the current position of the marking apparatus to the virtual entry position for this purpose.

The disclosed marking apparatus is typically introduced into the patient receiving region, in particular into the examination region, manually, in particular by medical staff.

The time-resolved MR image data is preferably acquired by means of the magnetic resonance device in real-time. The time-resolved MR image data typically maps the examination region, in particular the marking apparatus arranged inside the examination region and the entry position to be marked. The time-resolved MR image data is preferably three-dimensional. The time-resolved MR image data preferably comprises a plurality of slices, with the orientation of the plurality of slices being chosen in such a way that the entry position and the target position are encompassed by exactly one slice.

The marking apparatus, in particular the housing apparatus comprising MR-visible material and/or the liquid and/or a liquid comprising contrast medium, can be identified in the time-resolved MR image data. The current position of the marking apparatus preferably matches the position of the first longitudinal end of the marking apparatus in the time-resolved MR image data at a defined instant, preferably at the current instant, in other words real-time. The defined instant typically deviates from real-time by less than 3 seconds, preferably by less than 2 seconds, particularly preferably by less than 1 second. The current position is accordingly preferably ascertained in the coordinate system of the MR image data by means of the time-resolved MR image data.

The ascertainment of a current position of the marking apparatus preferably comprises a registering of the coordinate system of the MR image data with the time-resolved MR image data. The ascertainment of a current position of the marking apparatus preferably comprises a registering of the virtual entry position and/or the target position with the time-resolved MR image data. The ascertainment of a current position of the marking apparatus preferably comprises a visualization of the virtual entry position and/or the target position in combination with the time-resolved MR image data.

The iterative change in the current position of the marking apparatus using the virtual entry position and the current position preferably takes place manually in the position space, in other words in the coordinate system of the patient and/or of the magnetic resonance device.

The iterative change preferably comprises an approximation of the current position of the marking apparatus to the virtual entry position identifiable in the time-resolved MR image data, preferably shown combined with the virtual entry position.

When the current position of the marking apparatus matches the virtual entry position in the coordinate system of the MR image data the liquid is delivered to the surface, in particular the skin of the patient. For this purpose, the portioning apparatus of the marking apparatus is preferably manually controlled.

This method is intuitive and enables the medical staff to have complete control over the method for marking, so the acceptance for these methods on the part of medical staff is particularly high. In addition, the method enables significantly more precise marking and identification of the real entry position compared with marking using a finger. In addition, the marking can take place inside the examination region of the magnetic resonance device, so a movement of the patient between the identification and the marking of the entry position, for example owing to a movement of the patient and/or the patient supporting apparatus can be avoided. As a result, the method is more robust, faster and less dependent on the medical staff. Marking by means of stickers and a grid as well as counting grid lines can be omitted. Dispensing with a laser or a light source for generation of a light pattern reduces the costs. The use of time-resolved MR data enables checking of the marking in real-time, moreover, and a movement of the patient can be instantaneously compensated.

One aspect of the method provides that the acquisition of the time-resolved MR image data comprises an acquisition of projection image data. The projection image data can be acquired by actuation of the magnetic resonance device in accordance with a corresponding MR control sequence for projection mapping. The acquisition of projection image data is particularly fast, in particular compared with acquisition of three-dimensional MR image data, so the difference between a representation of the time-resolved MR image data and real-time is particularly small, so the iterative approach of the marking apparatus to the entry position can take place particularly continuously, intuitively and quickly.

One aspect of the method provides that the iterative change in the current position of the marking apparatus comprises the following method steps:
  ascertainment of a vector between the current position and the virtual entry position,
  visualization of the vector, the current position and the virtual entry position on a display unit,
  movement of the marking apparatus by taking into account the visualized vector.

The vector is typically determined in the coordinate system of the MR image data. The vector preferably describes a translation between the current position and the virtual entry position. The vector can comprise a line and/or a length and/or an indication of a distance. The vector typically connects the current position to the virtual entry position. The vector is preferably determined by way of comparison and/or formation of a difference between the current position and the virtual entry position. The vector is preferably visualized on a display unit of the magnetic resonance device designed as a monitor, which is typically arranged in the same space as the magnetic resonance device itself. This enables a particularly efficient and safe navigation of the marking apparatus since the medical staff can visually identify in which direction and/or how far the planned entry position is removed from the current position.

One aspect of the method provides that the provision of the virtual entry position comprises provision of a trajectory, which is taken into account on ascertainment of the vector. The trajectory preferably corresponds to the defined path for the medical instrument, in accordance with which path the target position can be reached by way of the entry position by taking into account anatomical boundary conditions. An angle of entry for the medical instrument can also be derived from the trajectory. In particular it is possible as a result to simulate as early as in the examination region, preferably with a marking apparatus having the same length as the medical instrument, whether the minimally invasive intervention can be achieved with the required angle of entry and/or the required trajectory. This increases the quality of the preparation of the minimally invasive intervention and therewith the safety of the patient.

One aspect of the method provides that the visualization of the vector comprises a representation of the time-resolved MR image data. The vector and/or the virtual entry position and/or the current position of the marking apparatus are typically illustrated in superposition in relation to MR image data. It is conceivable that the time-resolved MR image data is illustrated alternately to the vector. The representation in combination with the time-resolved MR image data, in particular in real-time, enables continuous feedback about positioning of the patient.

One aspect of the method provides that the iterative change in the current position of the marking apparatus also comprises output of a notification when the current position of the marking apparatus matches the virtual entry position. The notification can take place visually and/or audibly. The notification can typically be easily identified by the medical staff manually moving the marking apparatus and enables a continuous sequence of the method.

The advantages of the disclosed method for marking an entry position substantially match the advantages of the disclosed marking apparatus, which have been stated above in detail. Features, advantages or alternative aspects mentioned in this connection can likewise also be transferred to the other claimed subject matters, and vice versa.

Furthermore, the disclosure relates to a magnetic resonance device comprising an acquisition unit designed for acquisition of time-resolved MR image data and a control unit comprising an ascertainment unit, which is designed for ascertainment of a virtual entry position, and a determination unit, which is designed for ascertainment of a current position of a marking apparatus based on time-resolved MR image data. The disclosed magnetic resonance device is configured to support a disclosed method for marking an entry position for an injection apparatus.

For this, the control unit typically has an input, a processor unit and an output. The control unit can be provided via the input with functions, algorithms or parameters required in the method. The vector and/or the time-resolved MR image data and/or the virtual entry position and/or further results of an aspect of the disclosed method can be provided via the output. The control unit can be integrated in the magnetic resonance device. The control unit can also be installed separately from the magnetic resonance device. The control unit can be connected to the magnetic resonance device.

Aspects of the disclosed magnetic resonance device are designed analogously to the aspects of the disclosed method and the disclosed marking apparatus. The magnetic resonance device can have further control components, which are necessary and/or advantageous for carrying out a disclosed method. The magnetic resonance device can be designed to send control signals and/or to receive and/or process control signals in order to carry out a disclosed method. Computer programs and further software, by means of which the processor unit of the control unit automatically controls and/or carries out a process flow of a disclosed method, can be stored on a memory unit of the control unit.

A disclosed computer program product can be loaded directly into a memory unit of a programmable control unit and has program code means to carry out a disclosed method when the computer program product is executed in the control unit. As a result, the disclosed method can be carried out quickly, in an identically repeatable manner and robustly. The computer program product is configured such that it can carry out the disclosed method steps can by means of the control unit. The control unit has to have in each case the requirements such as, for example, an appropriate working memory, an appropriate graphics card or an appropriate logic unit, so the respective method steps can be efficiently carried out. The computer program product is stored for example on an electronically readable medium or on a network or server, from where it can be loaded into the processor of a local control unit, which can be directly connected to the magnetic resonance device or be designed as part of the magnetic resonance device. Furthermore, control information of the computer program product can be stored on an electronically readable data carrier. The control information of the electronically readable data carrier can be configured in such a way that it carries out a disclosed method when the data carrier is used in a control unit of a magnetic resonance device. Examples of electronically readable data carriers are a DVD, a magnetic tape a USB stick, on which electronically readable control information, in particular software, is stored. When this control information (software) is read from the data carrier and stored in a control unit of a magnetic resonance device, all disclosed aspects of the above-described method can be carried out.

The advantages of the disclosed magnetic resonance device and of the disclosed computer program product substantially match the advantages of the disclosed method for marking an entry position for an injection apparatus and the advantages of the disclosed marking apparatus, which have been stated above in detail. Features, advantages or alternative aspects mentioned in this connection can likewise also be transferred to the other claimed subject matters, and vice versa.

BRIEF DESCRIPTION OF THE DRAWINGS

Further advantages, features and details of the disclosure can be found in the exemplary aspects described below and with reference to the drawings, in which.

DETAILED DESCRIPTION

Figure 1:
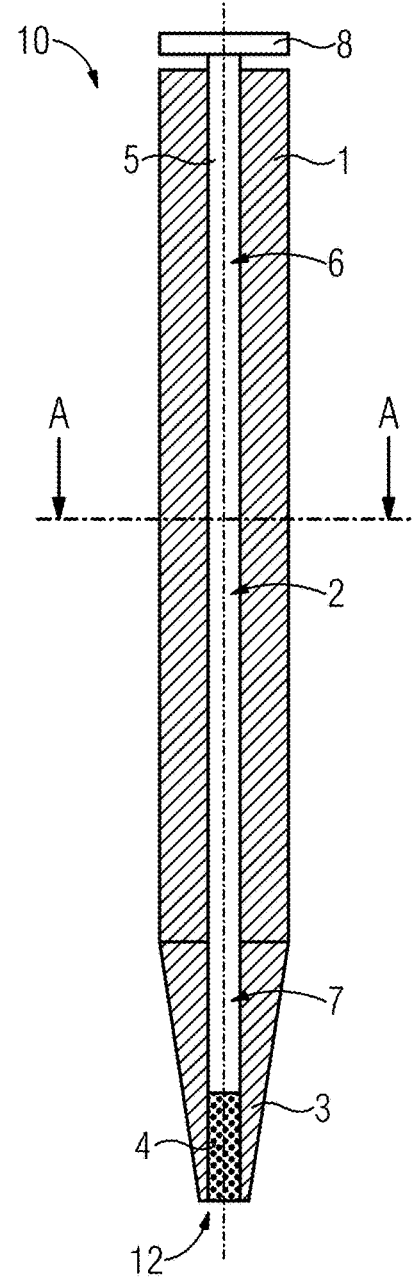
FIG. 1 shows a first aspect of a disclosed marking apparatus in a schematic representation in a first view.

FIG. 1 shows a first aspect of a disclosed marking apparatus comprising a tubular housing apparatus 1 made from MR-visible material in a first view. The longitudinal axis of the tubular housing apparatus 1 defines an axial direction. The housing apparatus 1 encloses a hollow region 2 oriented in the axial direction. The marking apparatus comprises a liquid apparatus 3, which is arranged inside the hollow region 2 at a first longitudinal end 12 of the housing apparatus. The liquid apparatus 3 is designed for acquisition and/or delivery of a liquid 4. The housing apparatus 1 comprises, moreover, a portioning apparatus 5, which is arranged inside the hollow region 2 and is designed for control of a volume of the liquid apparatus 3, so acquisition and/or delivery of the liquid 4 is checked.

The housing apparatus 1 preferably has a wall thickness that reduces in the direction of the first longitudinal end 12. The housing apparatus 1 may preferably be subdivided into a cylindrical part surrounding a first hollow region 6 and into a truncated cone-shaped part surrounding a second hollow region 7. The cylindrical part and the truncated cone-shape part typically adjoin in the axial direction and the truncated cone-shape part is arranged at the first longitudinal end 12. As a result, the second hollow region 7 is preferably also arranged at the first longitudinal end 12. In this aspect, the hollow region 2 comprises the first hollow region 6 and the second hollow region 7.

The second hollow region 7 may comprise the liquid apparatus. The portioning apparatus 5 is typically arranged inside the first hollow region 6. The length of the hollow region 2 in the axial direction typically matches the length of the housing apparatus 1.

The portioning apparatus 5 has external dimensions which are flush with the hollow region 2. The portioning apparatus 5 is movably arranged inside the hollow region 2.

The portioning apparatus 5 preferably has at the longitudinal end of the housing apparatus 1 opposing the first longitudinal end 12 a widening 8, which widening 8 is arranged outside of the housing apparatus 1.

Figure 2:
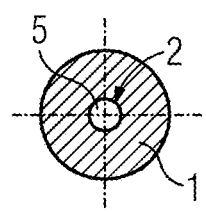
FIG. 2 shows a first aspect of a disclosed marking apparatus in a schematic representation in a second view.

FIG. 2 shows the first aspect of the disclosed marking apparatus in a second view. The second view shown in FIG. 2 matches the cross-section marked by A in FIG. 1. The hollow region 2 is preferably cylindrical. The tubular housing apparatus 1 preferably has a round periphery. The tubular housing apparatus 1 is accordingly preferably hollow cylindrical in shape.

Figure 3:
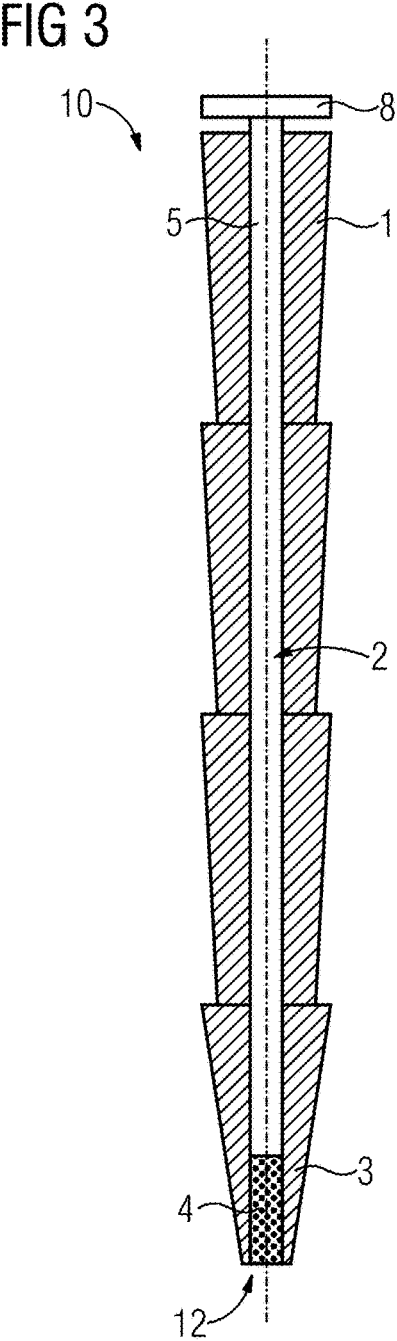
FIG. 3 shows a second aspect of a disclosed marking apparatus in a schematic representation.

FIG. 3 shows a second aspect of a disclosed marking apparatus in a schematic representation. The second aspect provides a variable length of the housing apparatus 1 in the axial direction, with the housing apparatus 1 being telescopic. The hollow region 2 is preferably cylindrical and also has a variable length.

Figure 4:
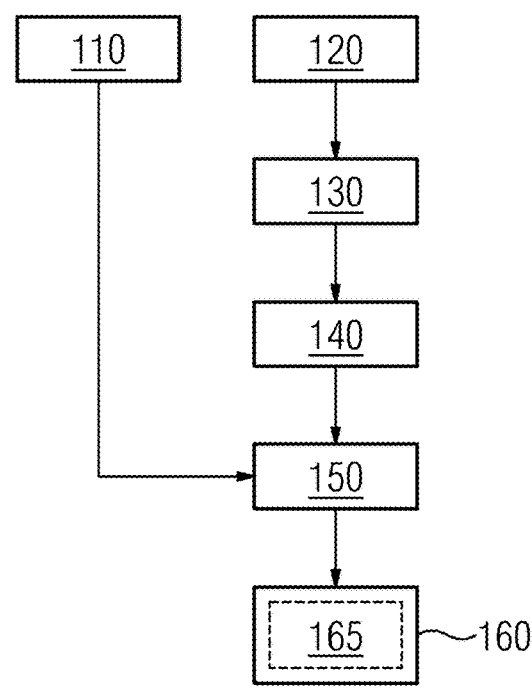
FIG. 4 shows a flowchart of a first aspect of a disclosed method.

FIG. 4 shows a flowchart of a first aspect of a disclosed method for marking an entry position 35 for an injection apparatus on a surface of a patient positioned inside a patient receiving region 14 of a magnetic resonance device. The method begins with method step 110, the provision of a virtual entry position. Method step 120, introducing a disclosed marking apparatus into the patient receiving region, typically takes place at the same time or subsequently. The following method step 130 comprises an acquisition of time-resolved MR image data from the marking apparatus by means of the magnetic resonance device. Typically, the marking apparatus and the entry position 35 are arranged in the patient receiving region 14. Method step 140 comprises the ascertainment of a current position of the marking apparatus based on the time-resolved MR image data. Method step 150 provides an iterative change in the current position of the marking apparatus using the virtual entry position and the current position. When the current position of the marking apparatus matches the virtual entry position, the liquid from the marking apparatus is delivered in method step 160. Optionally, when the current position of the marking apparatus matches the virtual entry position, a notification may also be output with method step 165.

Figure 5:
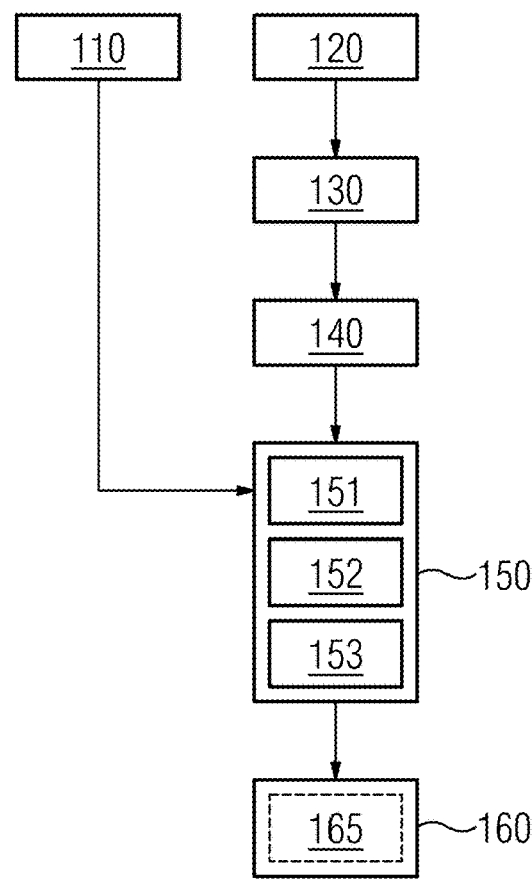
FIG. 5 shows a flowchart of a second aspect of a disclosed method.

FIG. 5 shows a flowchart of a second aspect of a disclosed method. The second aspect differs from the first aspect shown in FIG. 4 in method step 150, in other words the iterative change in the current position of the marking apparatus. Method step 150 comprises with method step 151 an ascertainment of a vector between the current position and the virtual entry position. In method step 152, the vector, the current position and the virtual entry position are visualized on a display unit 25 of the magnetic resonance device 11. Optionally, the time-resolved MR image data may also be displayed on the display unit 25. Method step 153 comprises a movement of the marking apparatus 10 by taking into account the visualized vector.

Figure 6:
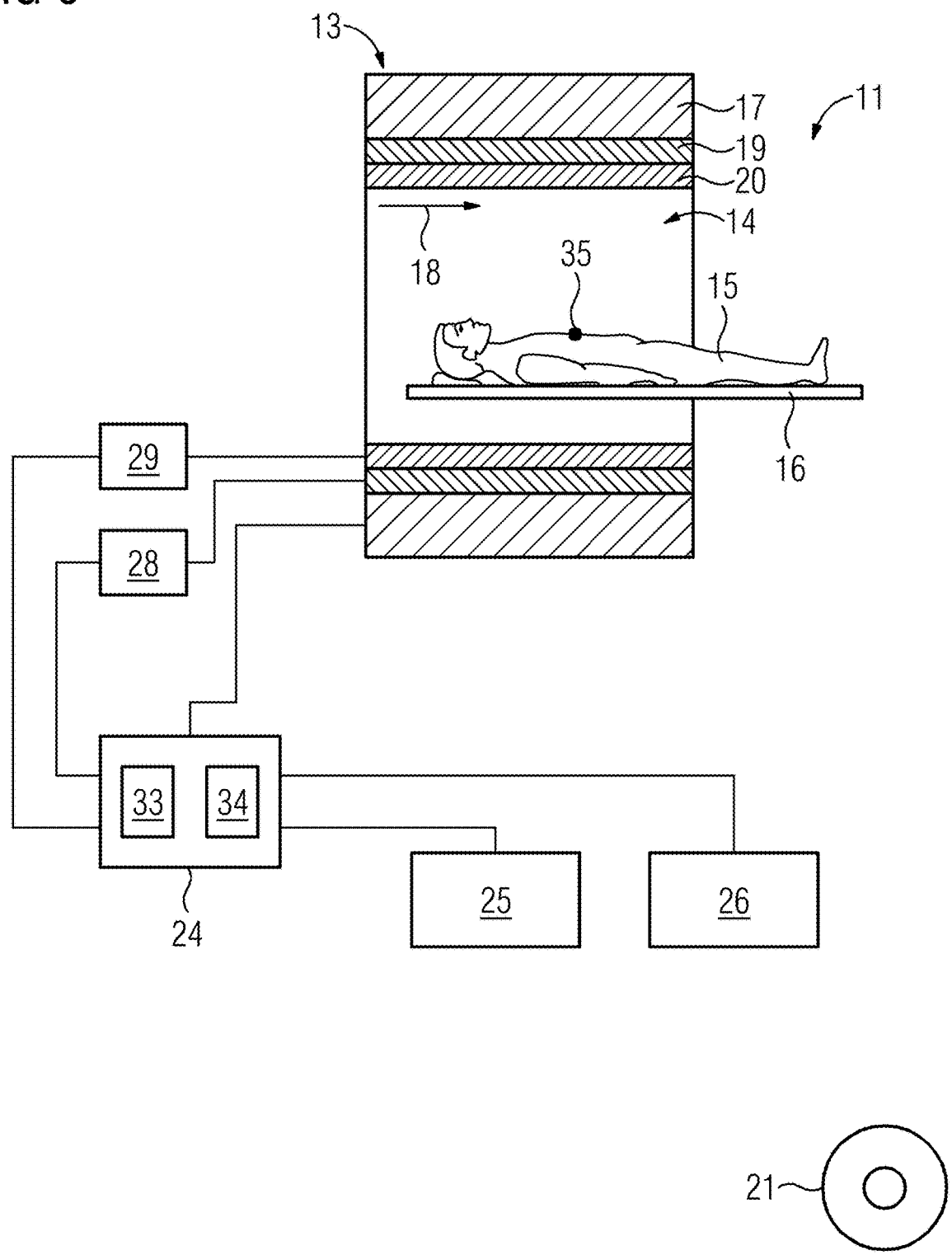
FIG. 6 shows a magnetic resonance device in a schematic representation.

FIG. 6 shows a magnetic resonance device 11 for supporting a disclosed method for marking an entry position for an injection apparatus in a schematic representation. The magnetic resonance device 11 comprises a detector unit formed by a magnet unit 13 with a main magnet 17 for generating a strong and, in particular, constant main magnetic field 18. In addition, the magnetic resonance device 11 has a cylindrical patient receiving region 14 for receiving a patient 15, with the patient receiving region 14 being cylindrically enclosed in a circumferential direction by the magnet unit 13. The patient 15 may be pushed by means of a patient supporting apparatus 16 of the magnetic resonance device 11 into the patient receiving region 14.

The magnet unit 13 also has a gradient coil unit 19, which are used for spatial encoding during imaging. The gradient coil unit 19 is actuated by means of a gradient control unit 28. Furthermore, the magnet unit 13 has a radio-frequency antenna unit 20 and a radio-frequency antenna control unit 29 for excitation of a polarization, which establishes itself in the main magnetic field 18 generated by the main magnet 17. The radio-frequency antenna unit 20 is actuated by the radio-frequency antenna control unit 29 and irradiates radio-frequency pulses into an examination space, which is formed substantially by the patient receiving region 14.

The magnetic resonance device 11 has a control unit 24 in order to control the main magnet 17, the gradient control unit 28 and the radio-frequency antenna control unit 29. The control unit 24 centrally controls the magnetic resonance device 11, such as carrying out MR control sequences. The control unit 24 together with the magnet unit 13 may be referred to as an acquisition unit. In addition, the control unit 24 comprises a reconstruction unit (not shown) for reconstruction of medical image data, which is captured during the magnetic resonance examination. The magnetic resonance device 11 has a display unit 25. Control information such as control parameters, as well as reconstructed image data may be displayed for a user on the display unit 25, for example on at least one monitor. In particular, the vector and/or the time-resolved MR image data and/or a notification when a current position of a marking apparatus matches a virtual entry position may be visualized on the display unit 25. In addition, the magnetic resonance device 11 has an input unit 26, by means of which information and/or control parameters may be input by a user during a measuring process. The control unit 24 may comprise the gradient control unit 28 and/or radio-frequency antenna control unit 29 and/or the display unit 25 and/or the input unit 26.

The control unit 24 also comprises a determination unit 33 and an ascertainment unit 34. The determination unit 33 is designed for ascertainment of a current position of a marking apparatus based on time-resolved MR image data. The ascertainment unit 34 is designed for an ascertainment of a virtual entry position.

For this purpose, the control unit 24 has computer programs and/or software, which may be loaded directly in a memory unit (not shown) of the control unit 24, with program means in order to carry out an ascertainment of a current position of a marking apparatus based on time-resolved MR image data and/or an ascertainment of a virtual entry position when the computer programs and/or software is/are executed in the control unit 24. The control unit 24 has for this purpose a processor (not shown), which is configured for execution of the computer programs and/or software. Alternatively, the computer programs and/or software may also be stored on an electronically readable data carrier 21 formed separately from the control unit 24, with data access from the control unit 24 to the electronically readable data carrier 21 being possible via a data network.

The illustrated magnetic resonance device 11 may of course comprise further components, which magnetic resonance devices 11 conventionally have. A general mode of operation of a magnetic resonance device 11 is known to a person skilled in the art, moreover, so a detailed description of the further components will be omitted.

Although the disclosure has been illustrated and described in detail by the preferred exemplary aspects, it is not limited by the disclosed examples and a person skilled in the art can derive other variations herefrom without departing from the scope of the disclosure.

The invention claimed is:

1. A marking apparatus, comprising:
  a tubular housing made from MR-visible material surrounding a hollow region oriented in an axial direction, wherein the tubular housing is telescopic and a length of the tubular housing is variable in the axial direction;
  a liquid apparatus, which is arranged inside the hollow region at a delivery end of the tubular housing, and is designed to receive and/or deliver a liquid; and
  a portioning apparatus, which is arranged inside the hollow region, and is designed to control a volume of the liquid apparatus to receive and/or deliver the liquid,
  wherein the tubular housing comprises telescoping sections arranged in the axial direction, each having a truncated cone shape with a decreasing diameter in a direction toward the delivery end, and wherein the telescoping sections are nestable within the telescoping section proximate the delivery end.

2. The marking apparatus as claimed in claim 1, wherein the hollow region is cylindrical.

3. The marking apparatus as claimed in claim 1, wherein the tubular housing has a wall thickness that decreases in a direction of the delivery end.

4. The marking apparatus as claimed in claim 1, wherein the hollow region comprises a first hollow region and a second hollow region, and the liquid apparatus corresponds to the second hollow region and is proximate the delivery end.

5. The marking apparatus as claimed in claim 1, wherein the portioning apparatus is arranged inside the first hollow region.

6. The marking apparatus as claimed in claim 1, wherein in the axial direction a length of the hollow region is equal to a length of the tubular housing.

7. The marking apparatus as claimed in claim 1, wherein the liquid comprises a contrast medium and/or the liquid is sterile and/or is colored.

8. The marking apparatus as claimed in claim 1, wherein the portioning apparatus has flush external dimensions and is movably arranged inside the hollow region.

9. The marking apparatus as claimed in claim 1, wherein the portioning apparatus at a longitudinal end of the tubular housing opposing the delivery end has a widening which is arranged outside of the tubular housing.

10. A method for marking an entry position for an injection apparatus on a surface of patient positioned inside a patient receiving region of a magnetic resonance device, the method comprising:
   providing a virtual entry position;
   introducing a marking apparatus as claimed in claim 1 into the patient receiving region;
   acquiring time-resolved magnetic resonance (MR) image data from the marking apparatus by the magnetic resonance device;
   ascertaining a current position of the marking apparatus based on the time-resolved MR image data;
   iteratively changing the current position of the marking apparatus using the virtual entry position and the current position; and
   delivering the liquid from the marking apparatus when the current position matches the virtual entry position.

11. The method as claimed in claim 10, wherein the acquisition of the time-resolved MR image data comprises acquiring projection image data.

12. The method as claimed in claim 10, wherein the iterative changing of the current position of the marking apparatus comprises:
   ascertaining a vector between the current position and the virtual entry position;
   visualizing the vector, the current position, and the virtual entry position on a display; and
   moving the marking apparatus taking into account the visualized vector.

13. The method as claimed in claim 12, wherein the provision of the virtual entry position comprises providing a trajectory, which is taken into account when ascertaining the vector.

14. The method as claimed in claim 12, wherein the visualization of the vector comprises representing the time-resolved MR image data.

15. The method as claimed in claim 10, wherein the iterative changing of the current position of the marking apparatus comprises outputting a notification when the current position of the marking apparatus matches the virtual entry position.

16. A magnetic resonance device, comprising:
   an acquisition unit designed to acquire time-resolved MR image data; and
   a control unit comprising:
   an ascertainment unit designed to ascertain a virtual entry position; and
   a determination unit designed to ascertain a current position of a marking apparatus based on time-resolved MR image data, which is configured to support a method for marking an entry position for an injection apparatus as claimed in claim 10.

* * * * *